(12) United States Patent
DeLegge

(10) Patent No.: US 8,632,492 B2
(45) Date of Patent: Jan. 21, 2014

(54) ENTERAL FEEDING TUBE AND HOUSING

(76) Inventor: Rebecca DeLegge, Mt. Pleasant, SC (US)

( * ) Notice: Subject to any disclaimer, the term of this patent is extended or adjusted under 35 U.S.C. 154(b) by 68 days.

(21) Appl. No.: 13/242,287

(22) Filed: Sep. 23, 2011

(65) Prior Publication Data

US 2012/0197191 A1    Aug. 2, 2012

Related U.S. Application Data

(60) Provisional application No. 61/462,189, filed on Jan. 31, 2011.

(51) Int. Cl.
*A61M 29/00*    (2006.01)

(52) U.S. Cl.
USPC ........................ 604/99.04; 604/174

(58) Field of Classification Search
USPC ................ 604/99.02–99.04, 97.01, 96.01, 74
See application file for complete search history.

(56) References Cited

U.S. PATENT DOCUMENTS

| | | | | |
|---|---|---|---|---|
| 5,342,321 A | * | 8/1994 | Potter | 604/174 |
| 6,322,539 B1 | * | 11/2001 | Cook | 604/174 |
| 7,699,817 B2 | * | 4/2010 | Adams | 604/246 |

* cited by examiner

*Primary Examiner* — Nicholas Lucchesi
*Assistant Examiner* — Melissa A Snyder
(74) *Attorney, Agent, or Firm* — B. Craig Killough; Barnwell Whaley Patterson & Helms, LLC

(57) ABSTRACT

An enteral feeding tube provides a conduit for the flow of liquid nutritional material. Most of the enteral feeding tube that is external to the patient is generally horizontal when the device is positioned in a stoma of a user lying in a prostrate position. A housing surrounds the horizontal portion enteral feeding tube, provides a low profile, aids in holding the enteral feeding tube in place, and protects the enteral feeding tube. The bottom surface of the housing comprises a resilient material that contacts the skin of the patient. The enteral feeding tube comprises a balloon that is positioned in the stomach to retain the device in the stomach. An air conduit extends generally vertically from an upper portion of the housing and through the enteral feeding tube to communicate with the balloon.

11 Claims, 4 Drawing Sheets

ENTERAL FEEDING TUBE AND HOUSING

Applicant claims the benefit of U.S. Provisional Patent Application Ser. 61/462,189 filed Jan. 31, 2011.

FIELD OF THE INVENTION

This invention relates to medical devices, and to methods and devices for feeding through gastrostomy feeding or access ports.

BACKGROUND OF THE INVENTION

Gastrostomy feeding devices provide access to the stomach from the exterior of the body through a stoma site. These devices are inserted and left in for the period of time that access to the stomach is needed, and are used as a conduit for feeding, decompression, delivery of medications, and suctioning of fluids.

Gastrostomy feeding devices provide means for connection to feeding delivery sets, or syringes used to access the gastrostomy. A lumen traverses the stoma into the stomach. If the connection is opened, reflux of gastric contents is likely. A valve may be positioned on the exterior of the stomach wall to prevent backflow of stomach contents. However, the valve and associated connectors and tubing are unsightly, and even frightening to children and other patients. Further, the tubular devices protrude vertically and materially from the exterior of the abdomen, and may interfere with sleep for the patient who sleeps on his or her stomach.

SUMMARY OF THE INVENTION

An enteral feeding tube provides a conduit for the flow of liquid nutritional material. Most of the enteral feeding tube that is external to the patient is generally horizontal when the device is positioned in a stoma of a user lying in a prostrate position. A housing surrounds the horizontal portion enteral feeding tube, provides a low profile, aids in holding the enteral feeding tube in place, and protects the enteral feeding tube. The bottom surface of the housing comprises a resilient material that contacts the skin of the patient. The enteral feeding tube comprises a retaining device, such as a bolster and/or balloon, which is positioned in the stomach to retain the device in the stomach. An air conduit extends generally vertically from an upper portion of the housing and through the enteral feeding tube to communicate with the balloon.

DETAILED DESCRIPTION OF PREFERRED EMBODIMENTS

Figure 1:
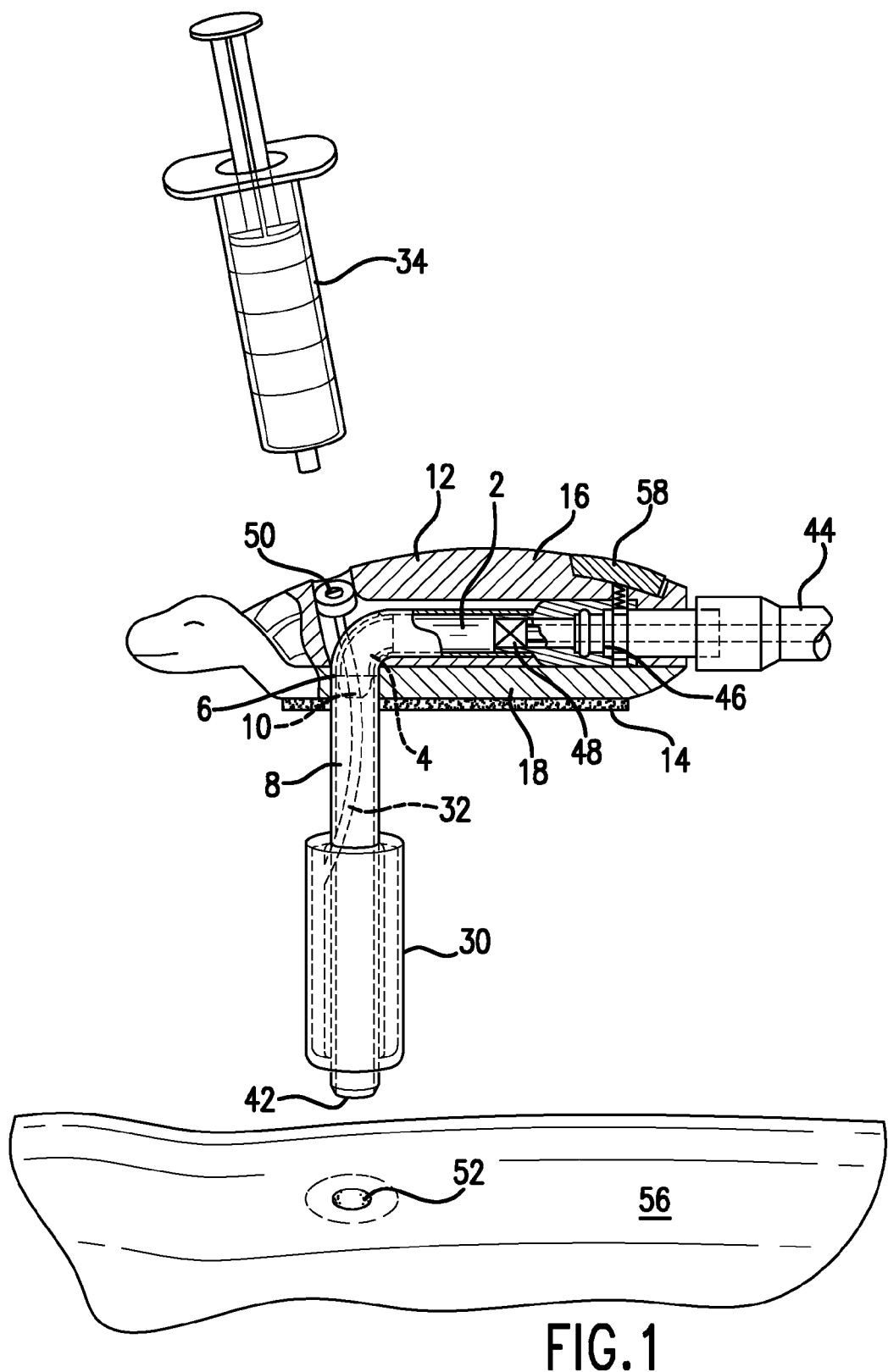
FIG. 1 is an embodiment of the enteral feeding tube according to the present invention positioned over a stoma site, with an inflation syringe shown over the enteral feeding tube construct.

Turning now to the drawing figures, the enteral feeding tube shown in FIG. 1 is positioned above, and is ready for entry into, a stoma site 52 surgically formed for access to a stomach 54 of a patient or user. The enteral feeding tube according to an embodiment of the present invention comprises a tube 2 that is positioned generally horizontally when present in a patient that is lying prostrate, and is generally horizontal to the surface of the skin of the patient, as demonstrated in the drawing figures. The feeding tube transitions to a generally vertical portion by an elbow 4. In a preferred embodiment, the elbow transitions the generally horizontal portion of the tube to the generally vertical portion of the tube, so that the elbow is preferred to be at generally a right angle. The elbow is further preferred to comprise an 80° to 100° angle between the generally horizontal tube and the generally vertical portion of the enteral feeding tube. The enteral feeding tube has a lumen therein which extends through from a first end of the tube to a second end of the tube, and provides a conduit to transport liquid nutritional material into the stomach.

Figure 2:
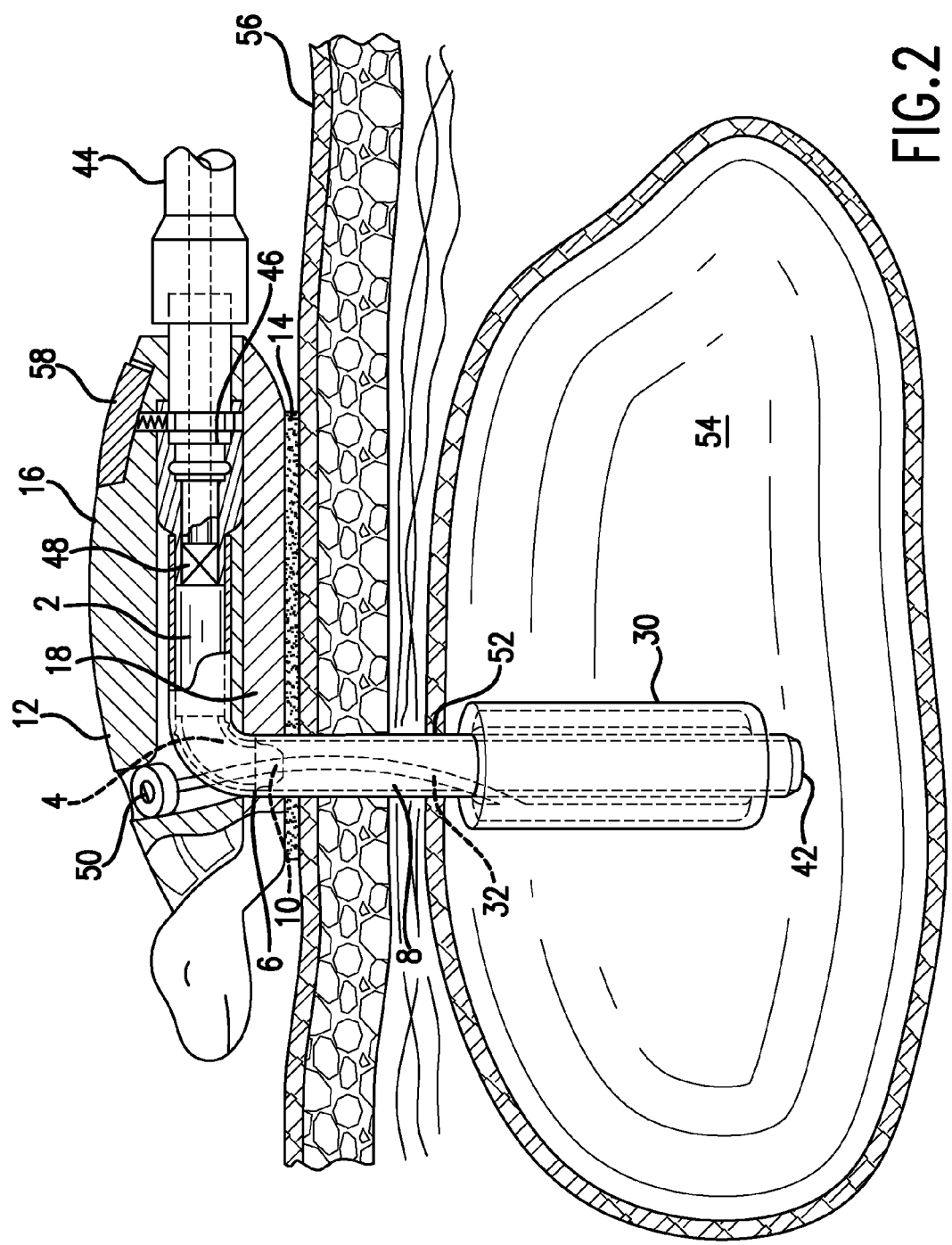
FIG. 2 is an embodiment of the enteral feeding tube according to the present invention positioned in the stoma site and stomach of a patient/user.

In a preferred embodiment, the generally vertical portion of the enteral feeding tube is formed in two (2) parts 6,8. A connector 10 connects and seals the two (2) parts, while providing a lumen as a conduit for the liquid nutritional material. The upper portion 6 of the generally vertical part of the feeding tube in one embodiment extends just past the elbow, and provides a horizontal connection point to tube 2 within the housing, as demonstrated in the drawing figures. The lower portion 8 of the generally vertical part of the enteral feeding tube extends from above the skin 56 of the patient and into the stomach of the patient. The connector, which may be a barbed-type connector, provides a connection between the two (2) parts of the generally vertical part of the enteral feeding tube. This connector permits the housing and the generally horizontal portion of the feeding tube to be removed, without requiring the portion of the feeding tube that is internal to the patient, as shown in FIG. 2, to be removed or materially disturbed.

The enteral feeding tube, when in use, extends generally horizontally as shown in the drawing figures and generally parallel to the skin of the user. The horizontal portion of the enteral feeding tube is not positioned materially above the body of the user. In a preferred embodiment, the horizontal portion of the feeding tube is within about 1.0 to 2.0 cm of the skin of the user when in position for use. The enteral feeding tube, by having most of its structure generally horizontal to the user at the point of entry of the tube into the user provides a feeding tube with a low profile, which is less likely to interfere with the patient's activities, including sleeping.

A housing 12 is provided that surrounds the portion of the enteral feeding tube that is external to the patient's body when the device is in position for use. The housing that surrounds the portion of the enteral feeding tube that is external to the patient's body protects the enteral feeding tube, and retards dislodging of the enteral feeding tube. The housing is preferred to have a soft and pliable lower pad 14 that contacts the patient's skin. The lower pad may be formed to be replaceable relative to the remaining body of the housing. The lower pad provides a comfortable interface between the housing and the skin. Particularly where the skin comprises a wound site, the pad encourages healing, and may provide a reservoir and/or comprise an absorbent material for transmission of medicaments to a wound site. The pad may be formed of resilient materials such as closed-cell foam, silicone or polyurethane. In keeping with the goal of the invention that the enteral feeding tube have a low profile through the use of the horizontal exterior portion of the feeding tube, the housing is preferred to have a low profile. The housing is also preferred to be formed in a shape that is artistic in appearance and form, and aesthetically pleasing, such as the shape of an animal, like the turtle shown, or a toy, such as a toy car, or in the shape of a plant. Such housings should have a low profile, with the preferred overall height of the housing being not more than 5.0 cm.

Figure 4:
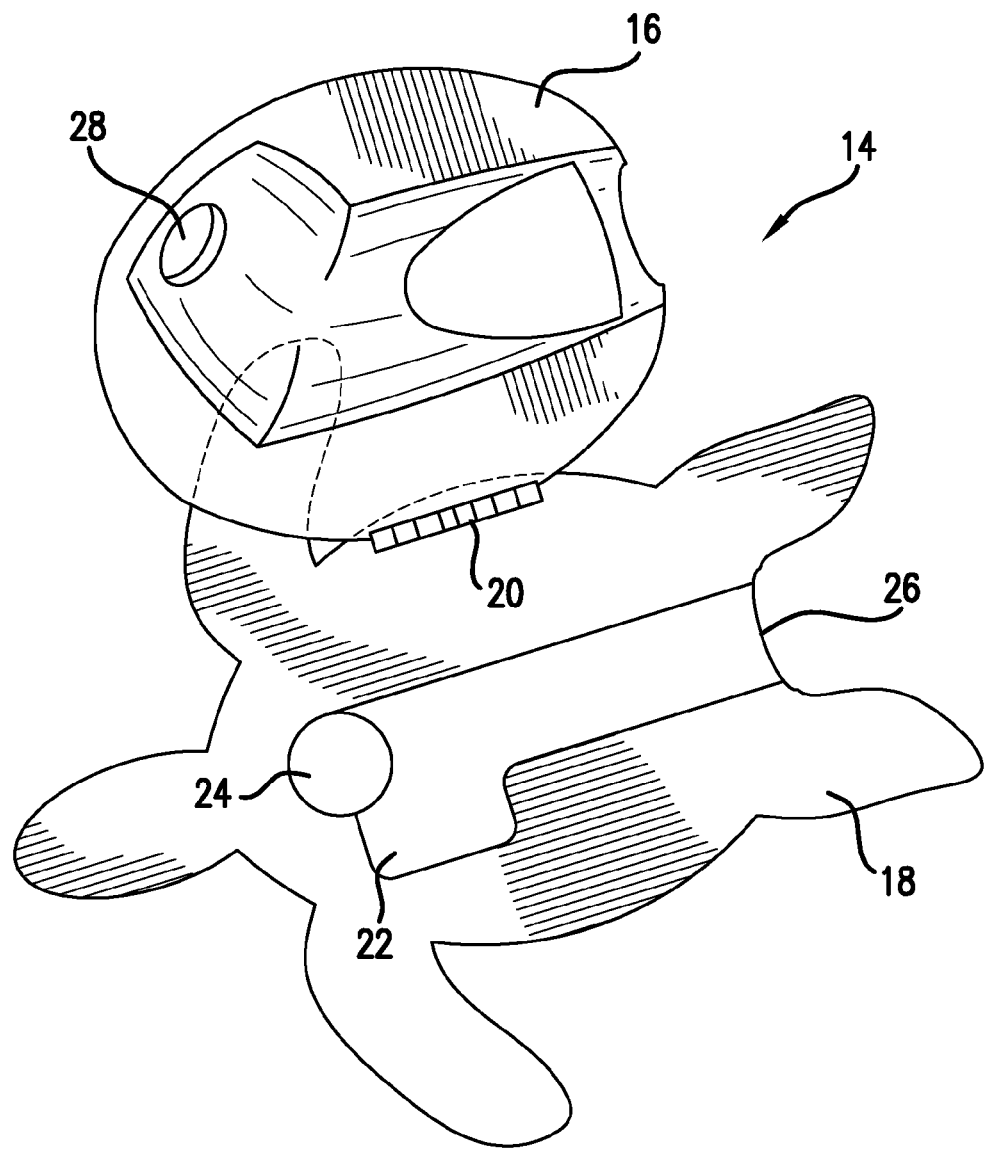
FIG. 4 shows an embodiment of a housing for the enteral feeding tube.

In a preferred embodiment, as shown in FIG. 4, the housing is formed in two (2) pieces, with a top portion 16 and a bottom portion 18. The top portion and the bottom portion may be hingeably connected, such as with a hinge 20, so that the generally horizontal portion of the enteral feeding tube and the elbow of the enteral feeding tube may be positioned and retained within the housing. The housing has a cavity 22 for holding the generally horizontal portion of the feeding tube, an opening 26 in an end of the housing for receiving a tube that transports nutritional material, and an opening 24 in the lower portion of the housing through which the elbow and the upper part of the generally vertical portion of the enteral feeding tube extend. An opening 28 for receiving the valve and inflation conduit may be provided. In the embodiment shown in FIG. 4, the housing may be pivoted to a closed position, or pivoted to an open position for insertion and removal of the enteral feeding tube. The enteral feeding tube may be located in the housing at the time of production, so that the device is provided to medical personnel in a ready to install form.

The enteral feeding tube is retained within the stomach by a balloon 30 that is inflated after the lower part of the generally vertical portion is inserted into the stomach of the patient. An inflation conduit 32 having a lumen therein extends from the upper portion of the housing and into the generally vertical portion of the enteral feeding tube and communicates with the balloon. A connector, such as a luer fitting and valve 50, may engage an inflation device such as a syringe 34, and air is forced through the lumen of the conduit into the balloon, whereupon the balloon inflates. Once the balloon is inflated, it retards the enteral feeding tube from being pulled from the stomach through the stoma site FIG. 3. The inflation conduit is positioned generally vertically when the patent is in the position lying prostrate, as shown in the drawing figures. The inflation conduit is preferred to be a relatively flexible tube.

The generally horizontal portion of the enteral feeding tube is preferred to be a hard plastic. The lower part 8 of the generally vertical portion of the enteral feeding tube is preferred to be a soft material, such as silicone.

Figure 3:
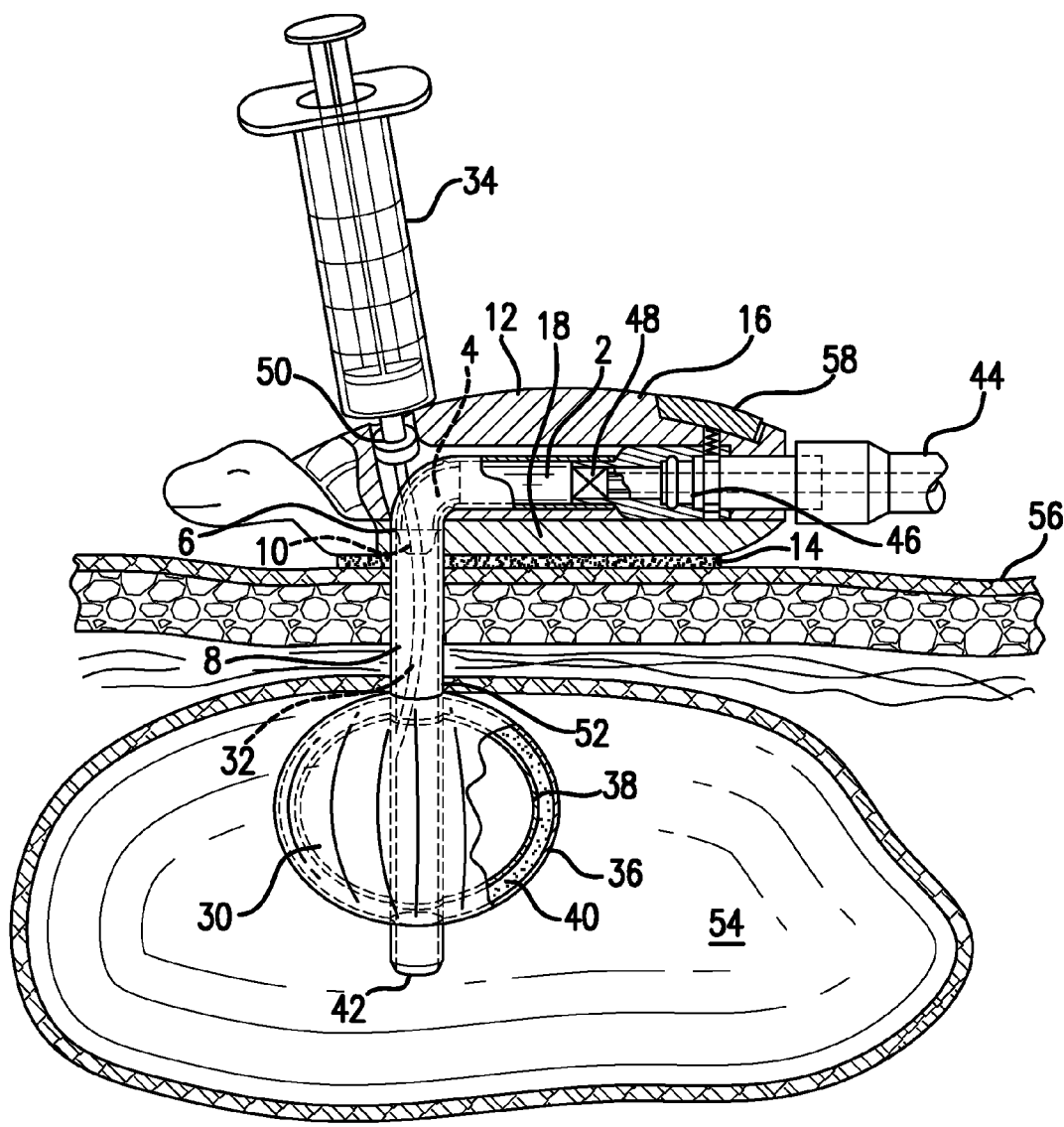
FIG. 3 is an embodiment of the enteral feeding tube according to the present invention positioned in the stoma site and stomach of a patient/user with an inflation syringe shown inflating the balloon of the enteral feeding tube.

As shown in FIG. 3, the balloon is preferred to be formed in two (2) or more layers. Using two (2) layers 36,38 to form the balloon reduces the likelihood of the balloon having or developing leaks due to manufacturing irregularities and/or stomach contents, such as the highly acidic environment of the stomach. In the preferred embodiment, not only is the balloon formed in two (2) layers, the balloon has a viscous, even semi-solid, and flowable material 40 that is present between the first layer and the second layer. This material will cover holes or similar disruptions in the surface of the layers of the balloon to inhibit air leakage from the balloon, and keep the balloon in an inflated state.

The lower part of the generally vertical portion of the enteral feeding tube has an opening 42 at the distal end to permit the liquid nutritional material to flow into the stomach to provide nutrition to the patient. The opposite end of the enteral feeding tube is present in an end of the generally horizontal portion of the enteral feeding tube and connects to a source 44 of liquid nutritional material. A fitting 46 is provided that joins and seals the food source to the generally horizontal portion of the enteral feeding tube. In a preferred embodiment, the fitting emits an audible click when the food source is joined to the enteral feeding tube and is properly sealed, so that that operator is certain of proper joinder between the food source conduit and the enteral feeding tube. A spring biased release button 58 may communicate with the fitting to release the horizontal portion of the enteral feeding tube from the source of nutritional material. The button is displacable by manual pressure relative to the housing, and is preferred to be positioned in the upper part of the housing.

In a preferred embodiment, a valve 48 is positioned within the generally horizontal portion of the enteral feeding tube. The valve permits a flow of liquid material into the enteral feeding tube, but prevents material from flowing from the stomach or otherwise through the valve.

What is claimed is:

1. An enteral feeding tube, comprising:
   a conduit comprising a valve, wherein a flow of fluid through the valve is generally horizontal when the valve is positioned in a stoma of a user lying in a prostrate position, wherein the conduit has an inlet and an outlet, and wherein a flow of fluid through the inlet is generally horizontal and a flow of the fluid from the outlet is generally vertical when the user is lying in the prostrate position;
   a housing, wherein the housing surrounds the valve and a horizontal portion of the conduit, wherein the housing is constructed and arranged to be removable from surrounding the horizontal portion of the conduit and the valve by the housing comprising a top and a bottom, and wherein the top and the bottom are connected;
   an inflation conduit that extends through the housing, and wherein the inflation conduit comprises an inflation valve that is accessible from the top of the housing when the top of the housing is positioned relative to the bottom of the housing so that the housing surrounds the horizontal portion of the conduit and the valve.

2. An enteral feeding tube as described in claim 1, wherein the bottom surface of the housing is constructed and arranged for contact with the user, and the bottom surface comprises a resilient material.

3. An enteral feeding tube as described in claim 1, wherein the housing constructed and arranged to be removable from surrounding the conduit and valve by the housing further comprises a releasable connector connecting the top to the bottom when the housing is positioned to surround the valve, and wherein the releasable connector comprises a release actuator that is accessible from the top of the housing.

4. An enteral feeding tube as described in claim 1, wherein the housing surrounding the valve and the horizontal portion of the conduit and constructed and arranged to be removable from surrounding the conduit and valve is formed in a shape that is artistic in appearance and form, and the shape of the housing is chosen from a group consisting of animal shapes, toy shapes and plant shapes.

5. An enteral feeding tube as described in claim 1, wherein the bottom of the housing is underneath the horizontal portion of the conduit and the valve and the top of the housing is over the horizontal portion of the conduit and the valve when the housing is in position to surround the horizontal portion conduit and valve.

6. An enteral feeding tube, comprising:
   a conduit comprising a valve, wherein a flow of fluid through the valve is generally horizontal when the valve is positioned in a stoma of a user lying in a prostrate position, wherein the conduit has an inlet and an outlet, and wherein a flow of fluid through the inlet is generally horizontal and a flow of the fluid from the outlet is generally vertical when the user is lying in the prostrate position;

a housing, wherein the housing surrounds the valve and a horizontal portion of the conduit, wherein the housing is constructed and arranged to be removable from surrounding the horizontal portion of the conduit and valve by the housing comprising a top and a bottom, and wherein the top and the bottom are hingeably connected, and wherein the top is pivotable relative to the bottom, wherein, when the top of the housing is positioned relative the bottom of the housing so that the housing surrounds the horizontal portion of the conduit and the valve, the height of the housing does not exceed 4.0 centimeters when the valve is positioned in a stoma of a user lying in a prostrate position.

7. An enteral feeding tube as described in claim 6, wherein the bottom surface of the housing is constructed and arranged for contact with the user, and the bottom surface comprises a resilient material.

8. An enteral feeding tube as described in claim 6, further comprising an inflation conduit that extends through the housing from the top of the housing to the bottom of the housing, and wherein the inflation conduit comprises an inflation valve that is accessible from the top of the housing when the top of the housing is positioned relative the bottom of the housing so that the housing surrounds the horizontal portion of the conduit and the valve.

9. An enteral feeding tube as described in claim 6, wherein the housing is constructed and arranged to be removable from surrounding the conduit and valve by the housing comprising a releasable connector connecting the top to the bottom when the housing is positioned to surround the valve, and wherein the releasable connector comprises a release actuator that is accessible from the top of the housing.

10. An enteral feeding tube as described in claim 6, wherein the housing surrounding the valve and the horizontal portion of the conduit and constructed and arranged to be removable from surrounding the conduit and valve is formed in a shape that is artistic in appearance and form, and the shape of the housing is chosen from a group consisting of animal shapes, toy shapes and plant shapes.

11. An enteral feeding tube as described in claim 6, wherein the bottom of the housing is underneath the horizontal portion of the conduit and the valve and the top of the housing is over the horizontal portion of the conduit and the valve when the housing is in position to surround the horizontal portion conduit and valve.

* * * * *